United States Patent
Giroldini et al.

(10) Patent No.: US 7,262,294 B2
(45) Date of Patent: Aug. 28, 2007

(54) PHOTOCHROMATIC PYRANO-1,3-OXAZINONAPHTHALENE DERIVATIVES

(75) Inventors: William Giroldini, San Donato Milanese (IT); Luciana Crisci, Graffignana (IT); Vincenzo Malatesta, San Maurizio al Lambro (IT)

(73) Assignee: Great Lakes Chemical (Europe) GmbH, Frauenfeld (CH)

( * ) Notice: Subject to any disclaimer, the term of this patent is extended or adjusted under 35 U.S.C. 154(b) by 696 days.

(21) Appl. No.: 10/257,408

(22) PCT Filed: Apr. 19, 2001

(86) PCT No.: PCT/EP01/04451

§ 371 (c)(1),
(2), (4) Date: Feb. 27, 2003

(87) PCT Pub. No.: WO01/81352

PCT Pub. Date: Nov. 1, 2001

(65) Prior Publication Data
US 2003/0164482 A1 Sep. 4, 2003

(30) Foreign Application Priority Data
Apr. 20, 2000 (IT) .................. MI2000A0885

(51) Int. Cl.
C07D 265/04 (2006.01)
C07D 265/12 (2006.01)
C07D 209/76 (2006.01)
C07D 209/78 (2006.01)
C08K 5/35 (2006.01)

(52) U.S. Cl. .................. 544/88; 544/88; 544/96; 544/71; 544/73; 252/586; 252/588; 524/89; 524/90; 524/96

(58) Field of Classification Search .................. 252/586
See application file for complete search history.

(56) References Cited

U.S. PATENT DOCUMENTS

| | | | | |
|---|---|---|---|---|
| 2,974,140 A | * | 3/1961 | Croxall et al. | 544/88 |
| 3,037,006 A | * | 5/1962 | Emmons et al. | 526/260 |
| 3,560,493 A | * | 2/1971 | Davis | 544/71 |
| 3,562,172 A | | 2/1971 | Ono et al. | |
| 3,578,602 A | | 5/1971 | Ono et al. | |
| 3,649,626 A | * | 3/1972 | Von Strandtmann et al. | 544/89 |
| 3,936,466 A | * | 2/1976 | Bodor et al. | 546/19 |
| 4,151,279 A | * | 4/1979 | Singer | 514/228.8 |
| 4,215,010 A | | 7/1980 | Hovey | |
| 4,342,668 A | * | 8/1982 | Hovey et al. | 252/586 |
| 5,110,922 A | * | 5/1992 | Castaldi et al. | 540/523 |
| 5,114,935 A | * | 5/1992 | Ballhause et al. | 514/228.8 |
| 5,186,867 A | * | 2/1993 | Castaldi et al. | 252/586 |
| 5,230,986 A | | 7/1993 | Neckers | |
| 5,608,065 A | * | 3/1997 | Melzig | 546/15 |

FOREIGN PATENT DOCUMENTS

| | | |
|---|---|---|
| EP | 0 625 518 | 11/1994 |
| EP | 0 629 620 | 12/1994 |
| JP | 05 009469 | 1/1993 |
| JP | 05 140549 | 6/1993 |

OTHER PUBLICATIONS

G. Berkovic et al.: "Spiropyrans and Spirooxazines for memories and switches" Chem. Reviews, vol. 100, No. 5, pp. 1741-1753 2000.

* cited by examiner

Primary Examiner—Joseph D. Anthony
(74) Attorney, Agent, or Firm—Oblon, Spivak, McClelland, Maier & Neustadt, P.C.

(57) ABSTRACT

Photochromatic compounds belonging to the groups of chromenes and spiro-pyrans having general formula (I)

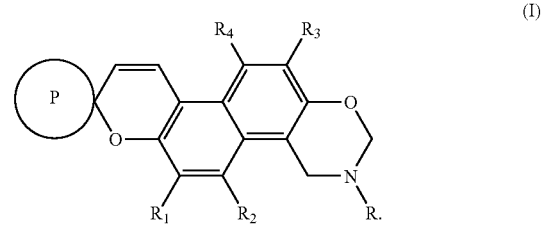

14 Claims, No Drawings

PHOTOCHROMATIC PYRANO-1,3-OXAZINONAPHTHALENE DERIVATIVES

This application is a 371 of PCT/EP01/04451, filed Apr. 19, 2001.

The present invention relates to photochromatic compounds belonging to the groups of chromenes and spiro-pyrans.

More specifically, the present invention relates to photochromatic compounds belonging to the groups of chromenes and spiro-pyrans containing a 1,3-oxazine-N-substituted ring in the molecule, a process for their preparation and their use in polymeric materials.

A further object of the present invention relates to polymeric compositions containing said photochromatic compounds and the photochromatic articles obtained from their processing.

Photochromatic compounds are substances which have the characteristic of reversibly changing colour and/or degree of light transmission when exposed to solar or artificial light in the band ranging from UV to visible, or to some types of electromagnetic radiation, returning to their original state of colour and transmission when the initial light source is removed.

There are numerous substances with photochromatic characteristics, which belong to various groups of both organic and inorganic compounds such as, for example, those described in the texts "Photochromism", by G. H. Brown (Ed.), Vol. III of the Weissberger series "Techniques of Organic Chemistry", Wiley Interscience, New York (1971) and in "Photochromism: Molecules and Systems", by H. Dürr and H. Bouas-Laurent (Ed.), Vol. 40 of the series "Studies in Organic Chemistry" Elsevier (1990).

Among organic photochromatic compounds, those belonging to the groups of spiro-indolino-oxazines, spiro-pyrans and chromenes, are particularly known and used.

The above compounds are capable of giving photochromatic characteristics to polymeric organic materials used, for example, in the production of photochromatic lenses for eye-glasses, special inks, toys, and in many other applications.

As an example, the following patents can be mentioned: U.S. Pat. No. 3,562,172, U.S. Pat. No. 3,578,602, U.S. Pat. No. 4,215,010, U.S. Pat. No. 4,342,668, U.S. Pat. No. 5,055,576, U.S. Pat. No. 5,110,922, U.S. Pat. No. 5,186,867, EP 146,135, EP 134,633, EP 141,407, EP 245,020, EP 0315,224 and IT 1,238,694.

The Applicant has now found photochromatic compounds belonging to the group of chromenes and spiro-pyrans containing a 1,3-oxazine-N-substituted ring in the molecule, which have excellent photochromatic characteristics, optimum wear resistance and high colourability characteristics.

An object of the present invention therefore relates to photochromatic compounds belonging to the group of chromenes and spiro-pyrans, having general formula (I):

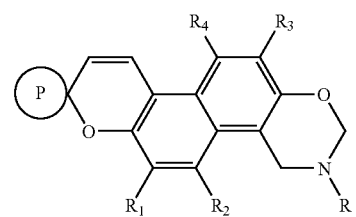

wherein:

R represents a linear or branched $C_1$-$C_{10}$ alkyl group, said alkyl group optionally substituted with 1-10 halogen atoms selected from fluorine, chlorine and bromine, aryl groups selected from phenyl, biphenyl and naphthyl, hetero-aromatic groups with 5-10 atoms, heterocyclic groups with 5-6 atoms, hydroxyl groups, carboxyl groups, cyano groups, linear or branched $C_1$-$C_6$ alkoxyl groups, or with a 1,2,2,6,6-pentamethylpiperidine group; a vinyl group; a (meth)allyl group; a linear or branched $C_2$-$C_6$ alkenyl group; an aryl group selected from phenyl, biphenyl and naphthyl, said aryl group optionally substituted with linear or branched $C_1$-$C_6$ alkoxyl groups, carboxyl groups, N,N-dialkyl-($C_1$-$C_6$)-amine groups; a $COOR'_a$ ester group wherein $R'_a$ represents a linear or branched $C_1$-$C_{10}$ alkyl group; a benzyl group, said benzyl group optionally substituted with 1-5 halogen atoms selected from fluorine, chlorine and bromine, or with $C(X')_3$ groups wherein X' is selected from fluorine, chlorine and bromine, linear or branched $C_1$-$C_{10}$ alkyl groups, linear or branched $C_1$-$C_6$ alkoxyl groups, carboxyl groups, cyano groups, or with a 1,2,2,6,6-pentamethylpiperidine group; or R represents a linear or branched $C_1$-$C_{10}$ alkyl group substituted with an ORy group wherein Ry represents a linear or branched hydroxy-($C_1$-$C_6$)-alkyl group, a (meth)allyl group, a (meth)acrylic group, a linear or branched carboxy-($C_1$-$C_6$)-alkyl group, an acyloxyl group, a group having general formula (II):

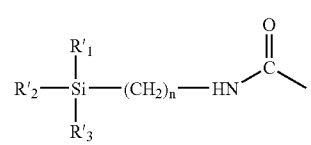

wherein $R'_1$, $R'_2$ and $R'_3$, the same or different, represent a hydrogen atom; a linear or branched $C_1$-$C_{10}$ alkyl group, said alkyl group optionally substituted with 1-10 halogen atoms selected from fluorine, chlorine and bromine, linear or branched $C_1$-$C_6$ alkoxyl groups, carboxyl groups, cyano groups, or with an N,N-dialkyl-($C_1$-$C_6$)-amine group, or with a cyclic amine; a vinyl group; a (meth)allyl group; a linear or branched $C_2$-$C_{10}$ alkenyl group; a $COOR'_a$ ester group wherein $R'_a$ represents a linear or branched $C_1$-$C_{10}$ alkyl group; a benzyl group, said benzyl group optionally substituted with 1-5 halogen atoms selected from fluorine, chlorine and bromine, or with $C(X')_3$ groups wherein X' is selected from fluorine, chlorine and bromine, linear or branched $C_1$-$C_{10}$ alkyl groups, linear or branched $C_1$-$C_6$ alkoxyl groups, carboxyl groups, cyano groups, or with a 1,2,2,6,6-pentamethylpiperidine group; a linear or branched $C_1$-$C_6$ alkoxyl group; an N,N-dialkyl-($C_1$-$C_6$)-amide group; and n is an integer ranging from 0 to 11, extremes included; or R represents one of the following groups having general formula (III), (IV) or (V):

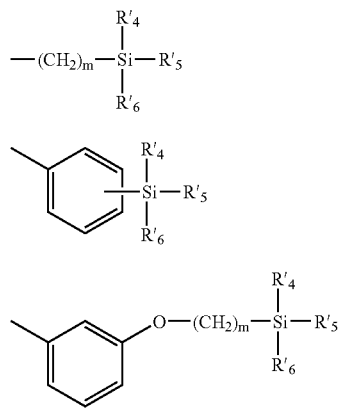

wherein $R'_4$, $R'_5$ and $R'_6$, the same or different, represent a linear or branched $C_1$-$C_{10}$ alkyl group; a linear or branched $C_1$-$C_6$ alkoxyl group; a hydroxyl group; a tri-alkyl-($C_1$-$C_6$)-siloxyl group; or a group having the formula: —O—($CH_2$)$_2$—O($CH_2$)$_2$—O$CH_3$; m is an integer ranging from 1 to 6, extremes included;

$R_1$, $R_2$, $R_3$ and $R_4$, the same or different, represent a hydrogen atom; a halogen atom selected from fluorine, chlorine, bromine and iodine; a linear or branched $C_1$-$C_{10}$ alkyl group, said alkyl group optionally substituted with 1-10 halogen atoms selected from fluorine, chlorine and bromine, linear or branched $C_1$-$C_6$ alkoxyl groups, ORx groups wherein Rx represents a linear or branched hydroxy-($C_1$-$C_6$)-alkyl group, carboxyl groups, hydroxyl groups, cyano groups, or with a 1,2,2,6,6-pentamethylpiperidine group; a benzyl group, said benzyl group optionally substituted with 1-5 halogen atoms selected from fluorine, chlorine and bromine, or with C(X')$_3$ groups wherein X' is selected from fluorine, chlorine and bromine, linear or branched $C_1$-$C_{10}$ alkyl groups, linear or branched $C_1$-$C_6$ alkoxyl groups, carboxyl groups, cyano groups, or with a 1,2,2,6,6-pentamethylpiperidine group; a hydroxyl group; a hydroxy-($C_1$-$C_6$)-alkyl group; a linear or branched $C_1$-$C_6$ alkoxyl group, said alkoxyl group optionally substituted with hydroxyl groups; an N,N-dialkyl-($C_1$-$C_6$)-amine group; a piperidine, piperazine or morpholine group; a $C_1$-$C_6$ carboxyalkyl group; a $C_2$-$C_6$ carboxyalkenyl group; a carboxyamide group; an N,N-dialkyl-($C_1$-$C_6$)-carboxyamide group; a cyano group; a nitro group; a sulfonic group; an aryl group selected from phenyl, biphenyl and naphthyl, said aryl group optionally substituted with N,N-dialkyl-($C_1$-$C_6$)-amine groups, linear or branched $C_1$-$C_6$ alkoxyl groups, hydroxyl groups, linear or branched $C_1$-$C_6$ alkyl groups; an acyl group of the alkyl ketone, aryl ketone or benzyl ketone type; a vinyl group; a (meth)allyl group; a (meth)acrylic group; a heteroallyl group; a linear or branched $C_2$-$C_6$ alkenyl group, said alkenyl group optionally substituted with one or two N,N-dialkyl-($C_1$-$C_6$)-4-aniline groups; an N-2,3-dihydroindoline group; a linear or branched $C_1$-$C_6$ thio-ether group;

two consecutive substituents between $R_1$, $R_2$, $R_3$ and $R_4$ can represent the condensation points with other aromatic, heterocyclic or quinonic rings;

P represents one of the following groups having general formula (VI) or (VII):

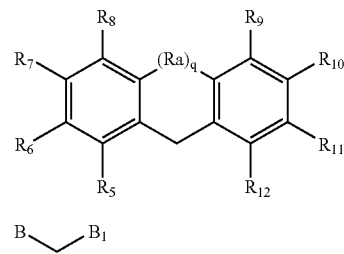

wherein $R_5$, $R_6$, $R_7$, $R_8$, $R_9$, $R_{10}$, $R_{11}$ and $R_{12}$, the same or different, have the same meanings as the $R_1$-$R_4$ substituents described above; two consecutive substituents between $R_5$ and $R_{12}$ can represent the condensation points with other aromatic, heterocyclic or quinonic rings; Ra represents a methylene group; a vinylene group; a carbon-carbon bond; q is 0, 1 or 2; B and $B_1$ are selected from the following groups: (i) aryl, phenyl and naphthalene groups, said aryl, phenyl and naphthalene groups optionally mono-, di- or tri-substituted; (ii) heterocyclic aromatic groups such as, for example, pyridyl, furanyl, benzofuran-2-yl, benzofuran-3-yl, thienyl, benzothien-2-yl, benzothien-3-yl, said heterocyclic aromatic groups optionally mono- or di-substituted; said aryl, phenyl, naphthalene and heterocyclic aromatic groups optionally being substituted with hydroxyl groups, piperidine groups, morpholine groups, pyrrole groups, linear or branched $C_1$-$C_6$ alkyl groups, linear or branched $C_1$-$C_6$ chloro-alkyl groups, linear or branched $C_1$-$C_6$ fluoro-alkyl groups, linear or branched $C_1$-$C_6$ alkoxyl groups optionally substituted with hydroxyl groups, linear or branched $C_1$-$C_4$ alkyl groups substituted with hydroxyl groups, linear or branched $C_1$-$C_6$ alkoxyl groups, acryloxyl groups, methacryloxyl groups, halogen atoms selected from chlorine and fluorine; (iii) groups represented by the following general formulae (VIII) or (IX):

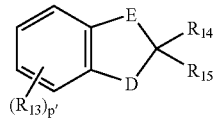

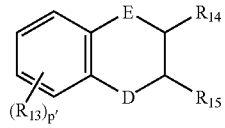

wherein E represents a carbon atom or an oxygen atom; D represents an oxygen atom or a substituted nitrogen atom, on the condition that, when D represents a substituted nitrogen atom, E represents a carbon atom, said nitrogen atom being substituted with linear or branched $C_1$-$C_6$ alkyl groups, or with $C_2$-$C_6$ acyl groups; $R_{13}$ represents a linear or branched $C_1$-$C_6$ alkyl group, a linear or branched $C_1$-$C_6$ alkoxyl group, a hydroxyl group, a halogen atom selected from chlorine and fluorine; $R_{14}$ and $R_{15}$ each independently represent a hydrogen atom, a linear or branched $C_1$-$C_6$ alkyl group; p' is 0, 1 or 2; (iv) linear or branched $C_1$-$C_6$ alkyl groups, linear or branched $C_1$-$C_6$ chloro-alkyl groups, linear or branched $C_1$-$C_6$ fluoro-alkyl groups, linear or branched $C_1$-$C_4$ alkyl groups substituted with linear or branched $C_1$-$C_6$ alkoxyl groups, $C_3$-$C_6$ cycloalkyl groups optionally mono-substituted with a linear or branched $C_1$-$C_6$ alkoxyl group or with a linear or branched $C_1$-$C_6$ alkyl group, or with a halogen atom selected from chlorine and fluorine; (v) a group having general formula (X):

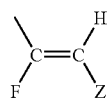

(X)

wherein F represents a hydrogen atom, a linear or branched $C_1$-$C_4$ alkyl group; and Z is selected from the following groups: naphthyl, phenyl, furanyl, thienyl, said naphthyl, phenyl, furanyl and thienyl groups, optionally mono- or di-substituted with linear or branched $C_1$-$C_4$ alkyl groups, linear or branched $C_1$-$C_4$ alkoxyl groups, halogen atoms selected from fluorine and chlorine; (vi) or, B and $B_1$ considered jointly, represent a fluoren-9-ylidene group, said fluoren-9-ylidene group optionally mono- or di-substituted with linear or branched $C_1$-$C_4$ alkyl groups optionally substituted with hydroxyl groups, linear or branched $C_1$-$C_4$ alkoxyl groups optionally substituted with hydroxyl groups, hydroxyl groups, halogen atoms selected from fluorine and chlorine, or they represent a group selected from spiro-monocyclic $C_3$-$C_{12}$ saturated hydrocarbon rings such as, for example, cyclopropylidene, cyclobutylidene, cyclopentylidene, cyclohexylidene, cycloheptylidene, cyclo-octylidene, cyclononylidene, cyclodecylidene, cycloundecylidene, cyclododecylidene; spiro-bicyclic $C_7$-$C_{12}$ saturated hydrocarbon rings such as, for example, bicyclo [2.2.1] heptylidene (norbornylidene), 1,7,7,-trimethyl-bicyclo [2.2.1]heptylidene (bornylidene), bicyclo[3.2.1]octylidene, bicyclo-[3.3.1]nonan-9-ylidene, bicyclo[4.3.2] undecane; spiro-tricyclic $C_7$-$C_{12}$ saturated hydrocarbon rings such as, for example, tricyclo[2.2.1.0$^{2,6}$]heptylidene, tricyclo [3.3.1.1$^{3,7}$]decylidene (adamantylidene), tricyclo[5.3.1.1$^{2,6}$]dodecylidene.

Preferred photochromatic compounds having general formula (I) for the purposes of the present invention are those wherein:

R represents one of the following groups: methyl, ethyl, isopropyl, 2-(meth)allyl, 2-carboxymethyl, phenyl, 4-N, N-dimethylaminoaniline, 4-methoxybenzene, 4-cyanobenzene, 2-methoxyethyl ($-CH_2CH_2OCH_3$), hydroxyalkyl such as ($-CH_2OH$) or ($-CH_2CH_2OH$),; or it represents an alkyl group substituted with an ORy group wherein Ry represents a (meth)acrylic group; a group having general formula (II) wherein R'$_1$, R'$_2$ and R'$_3$, the same or different, represent a methoxyl group or an ethoxyl group and n is 3; or it represents a group having general formula (III), (IV) or (V), wherein R'$_4$, R'$_5$ and R'$_6$, the same or different, represent one of the following groups: methyl, hydroxyl, methoxyl, ethoxyl, an $-O-(CH_2)_2-O(CH_2)_2-OCH_3$, group, or a tri-methylsiloxyl group and m ranges from 2 to 6, extremes included;

$R_1$, $R_2$, $R_3$ and $R_4$, the same or different, represent a hydrogen atom, a fluorine atom, a chlorine atom, a bromine atom, or one of the following groups: methyl, isopropyl, hydroxyl, 2-hydroxyethyl, methoxyl, N,N-dimethylamine, piperidine, morpholine, carboxyl, carboxymethyl, N,N-dimethyl-carboxyamide, cyano, nitro, methylketone, phenylketone, phenyl, ORx wherein Rx represents 2-hydroxyethyl;

P represents one of the groups having general formula (VI) or (VII) wherein:

$R_5$, $R_6$, $R_7$, $R_8$, $R_9$, $R_{10}$, $R_{11}$ and $R_{12}$, have the same meanings as $R_1$, $R_2$, $R_3$ and $R_4$ described above;

two consecutive substituents between $R_3$ and $R_{10}$ can represent the condensation point with other aromatic, heterocyclic or quinonic rings;

Ra represents a carbon-carbon bond;

q is 0;

B and $B_1$, are each independently selected from the following groups: (i) phenyl groups optionally mono- or di-substituted; (ii) heterocyclic aromatic groups such as, furanyl, benzofuran-2-yl, thienyl, benzothien-2-yl, said heterocyclic aromatic groups optionally mono- or di-substituted; said phenyl and heterocyclic aromatic groups being optionally substituted with hydroxyl groups, linear or branched $C_1$-$C_3$ alkyl groups, $C_1$-$C_2$ hydroxyalkyl groups, linear or branched $C_1$-$C_3$ alkoxyl groups, halogen atoms selected from chlorine and fluorine; (iii) groups represented by general formula (VIII) wherein E represents a carbon atom, D an oxygen atom; $R_{13}$ represents a linear or branched $C_1$-$C_3$ alkyl group, a linear or branched $C_1$-$C_3$ alkoxyl group; $R_{14}$ and $R_{15}$ each independently represent a hydrogen atom, a linear or branched $C_1$-$C_3$ alkyl group,; p' is 0 or 1; (vi) or, B and B' considered jointly, represent a fluoren-9-ylidene group, or a group selected from: adamantylidene, bornylidene, norbornylidene, bicyclo [3.3.1]nonan-9-ylidene.

Specific examples of preferred compounds according to the present invention, but which should in no way be considered as limiting its scope, are:

The compound having formula (Ia):
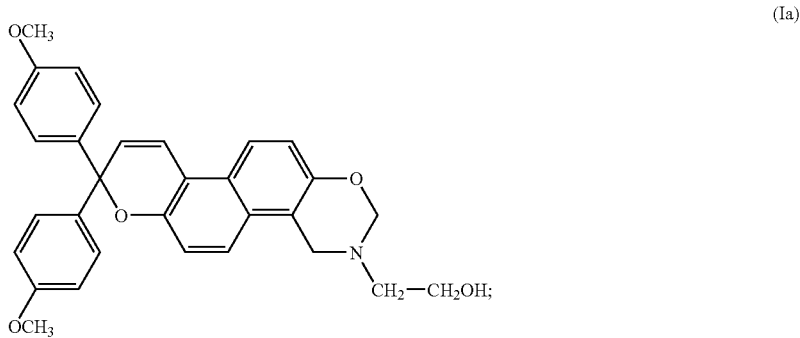
The compound having formula (Ib):
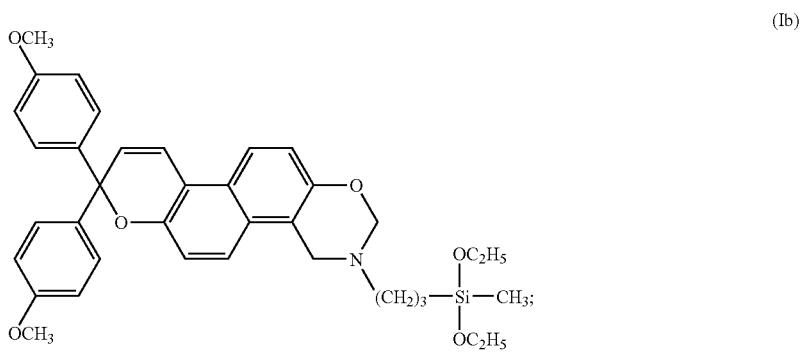
The compound having formula (Ic):
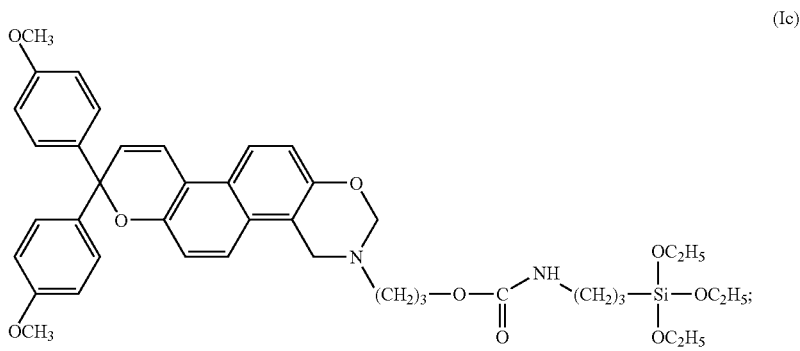
The compound having formula (Id):
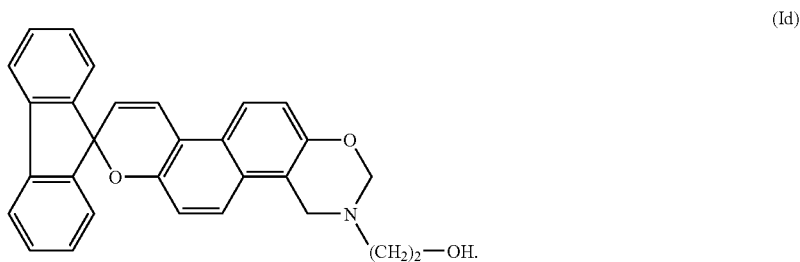

A further object of the present invention relates to a process for the preparation of the photochromatic compounds having general formula (I).

The photochromatic compounds having general formula (I) can be prepared by the condensation of photochromatic compounds having general formula (XI):

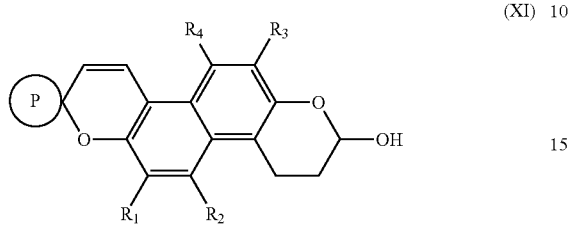

wherein $R_1$, $R_2$, $R_3$, $R_4$ and P have the same meanings defined above, with amines having general formula (XII):

H$_2$N—R  (XII)

wherein R has the same meanings described above, in the presence of formaldehyde, an inert organic solvent such as, for example, ethanol, acetonitrile, etc., at a temperature ranging from 50° C. to 80° C., preferably at 60° C., for a time ranging from 1 hour to 15 hours, preferably from 1 to 6 hours.

The reaction product thus obtained, corresponding to one of the photochromatic compounds having general formula (I), is purified by means of crystallization, or by elution on a silica column.

Examples of amines having general formula (II) are: 2-hydroxyethylamine, 3-hydroxypropylamine, 3-aminopropylmethyldiethoxysilane, p-aminophenyltrimethoxysilane, 3-(2-aminophenoxy)propyltrimethoxysilane, etc.

The photochromatic compounds having general formula (XI) are obtained by the condensation of compounds deriving from propargyl alcohol having general formula (XIII), or of compounds deriving from α,β-unsaturated aldehydes having general formula (XIV), with hydroxy-aryl compounds having general formula (XV), to give the photochromatic compounds having general formula (XI), indicated in Schemes 1-2:

SCHEME 1

-continued

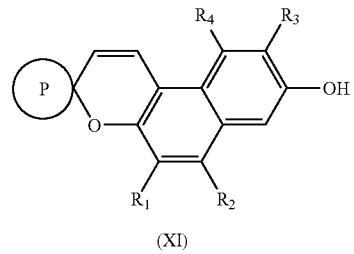

SCHEME 2

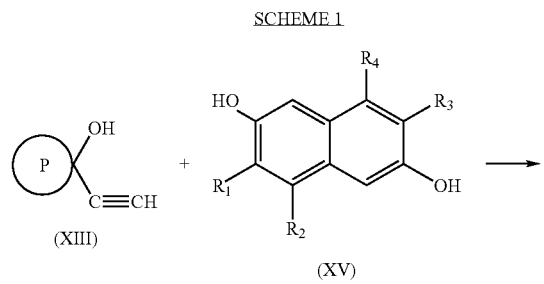

wherein the substituents $R_1$, $R_2$, $R_3$, $R_4$ and P have the same meanings defined above.

Said condensation reaction is carried out in the presence of an inert organic solvent such as, for example, ethyl alcohol, isopropanol, toluene, or a mixture of said solvents, and in the presence of an amine such as, for example, triethylamine, methylmorpholine, piperidine, or an acid such as, for example, paratoluenesulfonic acid, sulfuric acid, acid alumina, or a metallic complex such as, for example, titanium(IV)tetra-ethoxide, as catalyst, at a temperature ranging from 50° C. to 100° C., preferably from 60° C. to 75° C., for a time ranging from 1 hour to 10 hours, preferably from 2 hours to 3 hours. The reaction product thus obtained is generally purified by means of elution on a silica column and subsequent crystallization from a solvent such as, for example, acetone, toluene, hexane, heptane, pentane, diethyl ether.

The compounds deriving from propargyl alcohol having general formula (XIII) can be prepared by the reaction of ketone compounds with sodium acetylide in xylene or with a lithium acetylide/ethylenediamine complex as described, for example, in U.S. Pat. Nos. 5,585,042 and 5,238,981.

The compounds deriving from α,β-unsaturated aldehydes having general formula (XIV) can be prepared according to processes known in the art as described, for example, in Japanese patent application JP 48/016482; or in "Organic Synthesis" (1970), Vol. 50, page 66.

The hydroxy-aryl compounds having general formula (XV) are usually products which are commercially available such as, for example, 2,6-dihydroxynaphthol.

Specific examples of derivatives of propargyl alcohol having general formula (XIII) are the following:

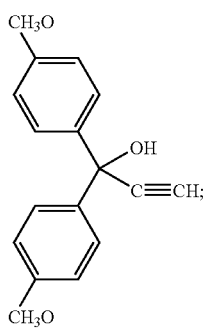

(XIII)-1

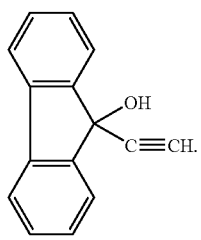

(XIII)-2

Specific examples of α,β-unsaturated aldehydes having general formula (XIV) are the following:

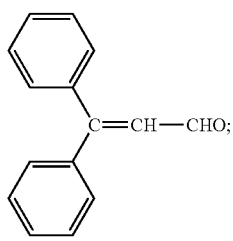

(XIV)-1

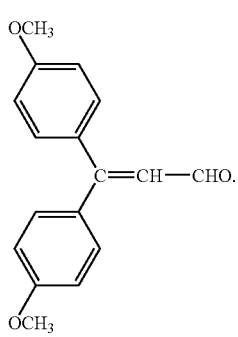

(XIV)-2

Specific examples of hydroxy-aryl compounds having general formula (XV) are the following:

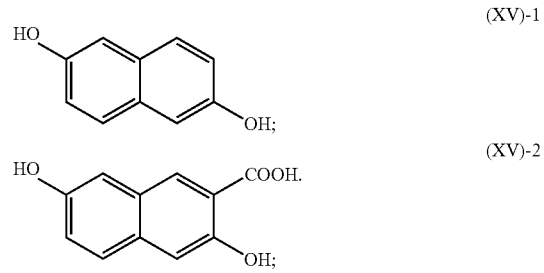

(XV)-1

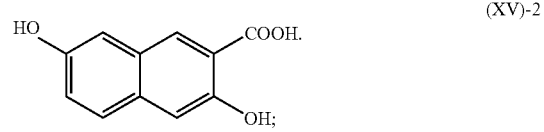

(XV)-2

The photochromatic compounds having general formula (I), object of the present invention, are colourless or lightly coloured powders.

Their solutions in common organic solvents, such as benzene, toluene, methanol, ethanol, for example, when not exposed to light sources, are colourless or slightly amber-coloured. When said solutions are exposed to a light source, either visible or ultraviolet, they become yellow-orange coloured, or pink. The colouring rapidly fades when the light source is removed.

The photochromatic compounds having general formula (I), object of the present invention, can be applied to the surface or incorporated in mass into the desired articles, using techniques already known in the art and described hereunder.

Some polymeric photochromatic end-articles can be obtained with moulding techniques such as, for example, injection or compression moulding, starting from polymers in which one or more of the photochromatic compounds in the solid state having formula (I) are homogeneously dispersed in mass.

Alternatively, the photochromatic compounds having general formula (I) can be dissolved in a solvent, together with the polymeric material such as, for example, polymethyl methacrylate, polyvinyl alcohol, polyvinyl butyral, cellulose acetate butyrate or epoxy, polysiloxane, urethane resin.

The mixture thus obtained is deposited on a transparent base to form, after evaporation of the solvent, a photochromatic coating.

The photochromatic compounds having general formula (I) described above, can also be added to a polymerizable monomer such as, for example, a meth(acrylic) or allyl carbonate monomer, so that, after polymerization carried out in the presence of a suitable initiator such as, for example, azo-bis (isobutyronitrile) in the case of the meth(acrylic) monomer, or a peroxyketal in the case of the allyl carbonate monomer, they are uniformly incorporated in the resin formed.

Finally, the photochromatic compounds having general formula (I) can be applied to a transparent substrate such as, for example, polycarbonate, polymethyl methacrylate or polydiethyleneglycol bis(allyl carbonate), by means of surface impregnation obtained by putting the substrate in contact, at a suitable temperature, with a solution or dispersion containing one or more of the photochromatic compounds having general formula (I), operating according to a known method described, for example, in U.S. Pat. No. 5,130,353.

The photochromatic compounds having general formula (I), object of the present invention, have the characteristic of being able to be incorporated in mass, or using one of the techniques described above, into various organic polymers such as, for example, high density polyethylene (HDPE), low density polyethylene (LDPE), ethylene-vinylacetate copolymer, polyether amides, polypropylene, polymethyl methacrylate, polyvinyl alcohol, polyvinyl butyral, cellulose acetate butyrate, epoxy, polysiloxane or urethane resins, polycarbonate, polydiethylene glycol bis(allyl carbonate), polyamides, polyesters, polystyrene, polyvinylchloride, polyethylacrylate, siliconic polymers.

A further object of the present invention therefore relates to polymeric compositions comprising the above polymeric materials and the above photochromatic compounds having general formula (I) and the photochromatic articles obtained from their processing.

The photochromatic compounds having general formula (I), object of the present invention, are added to the above polymeric compositions in a quantity ranging from 0.01% to 5% by weight, preferably between 0.1% and 2% by weight, with respect to the weight of said polymeric compositions.

The photochromatic compounds having general formula (I), object of the present invention, can also be added to coating compositions, such as for example, paints, lacquers, paints or lacquers based on hybrid polysiloxanes and/or silica gel, compositions based on plastic materials.

A further object of the present invention therefore relates to coating compositions, such as for example, paints, lacquers, paints or lacquers based on hybrid polysiloxanes and/or silica gel, compositions based on plastic materials, comprising said photochromatic compounds.

The photochromatic compounds having general formula (I), object of the present invention, are added to the above coating compositions in a quantity ranging from 0.01% to 12% by weight, preferably between 0.1% and 4% by weight, with respect to the weight of said coating compositions.

Paints or lacquers based on hybrid polysiloxanes and/or silica gel are obtained by means of the "sol-gel" process described, for example, by M. Nogami, Y. Abe in: "Journal of Materials Science" (1995), Vol. 30, pages 5789-5792.

The above coating compositions can be applied to the substrate (metal, plastic, wood, etc.) using the conventional methods such as, for example, brushing, spraying, pouring, dipping or electrophoresis.

The photochromatic compounds having general formula (I), object of the present invention, can optionally be used in the presence of the usual additives for organic polymers such as, for example, phenolic antioxidants, sterically hindered amines, benzotriazoles, benzophenones, phosphites or phosphonites, enamines.

The photochromatic compounds having general formula (I), object of the present invention, which, as already specified above, are colourless or have a light colouring, can be used as such, mixed with each other, or in a combination with other suitable organic photochromatic compounds in order to obtain, after activation, the formation of colourings such as brown and grey. Particularly useful for this purpose are photochromatic compounds belonging to the group of spiro-indoline-oxazines or spiro-pyrans described in the art, for example, in U.S. Pat. No. 5,066,818.

Some illustrative examples are provided for a better understanding of the present invention and for its embodiment but should in no way be considered as limiting the scope of the invention itself.

EXAMPLE 1

Preparation of the Compound Having Formula (XIII)-1

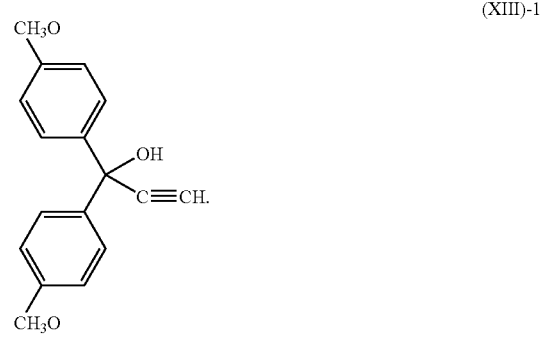

(XIII)-1

48 g of 4,4'-dimethoxybenzophenone and 90 ml of tetrahydrofuran are charged into a 250 ml flask, equipped with a reflux cooler and mechanical stirrer. 80 g of a suspension of sodium acetylide in xylene at 18% are added, under stirring, to the solution, obtaining a mixture which is saturated with gaseous acetylene and left at 40° C. for 16 hours.

The above mixture is subsequently cooled to room temperature and 125 ml of water and 250 ml of toluene are added. The toluene phase is separated and concentrated, obtaining 50 g of a white crystalline precipitate corresponding to the compound having formula (XIII)-1 which is identified by means of gas-mass (molecular weight: 242.27).

EXAMPLE 2

Preparation of the Compound Having Formula (XI)-1.

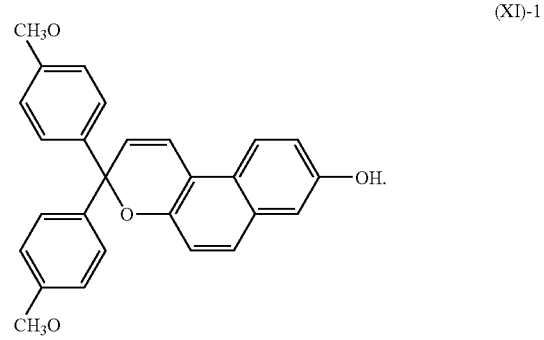

(XI)-1

10 g of 2,6-dihydroxynaphthalene having formula (XV)-1, 17 g of the Compound having formula (XIII)-1 obtained as described in Example 1, 90 ml of methylethylketone and 1 ml of trifluoroacetic acid are charged into a 200 ml flask equipped with a reflux cooler and mechanical stirrer: the mixture is left, under stirring, at 25° C. for 6 hours.

10 g of activated carbon and 50 ml of toluene are added to the reaction raw product obtained: the mixture is heated to 60° C. for 1 hour. The organic phase is subsequently filtered and concentrated and the raw product obtained is recrystallized twice with 100 ml. of toluene obtaining 11.2 g of a product corresponding to the Compound having formula (XI)-1 which is identified by means of gas-mass (molecular weight=410).

EXAMPLE 3

Preparation of the Compound Having Formula (Ia).

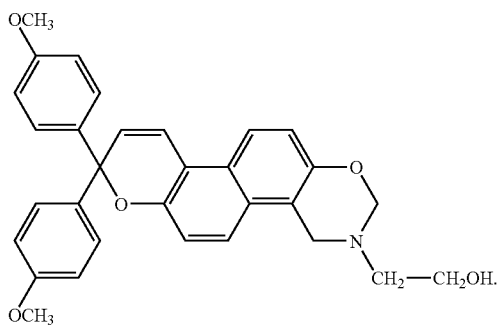

(Ia)

4.10 g of the Compound having formula (XI)-1 obtained as described in Example 2, 0.84 g of formaldehyde, 25 ml of ethanol and 0.84 g of 2-hydroxyethylamine are charged into a 50 ml flask equipped with a bubble cooler and magnetic stirrer: the mixture is heated to reflux temperature for 2 hours.

A white precipitate is obtained, which is cooled to room temperature, filtered and washed with ethanol (20 ml) obtaining 3.25 g of a product corresponding to the Compound having formula (Ia) which is identified by means of gas-mass (molecular weight=495).

EXAMPLE 4

Preparation of the Compound Having Formula (Ib).

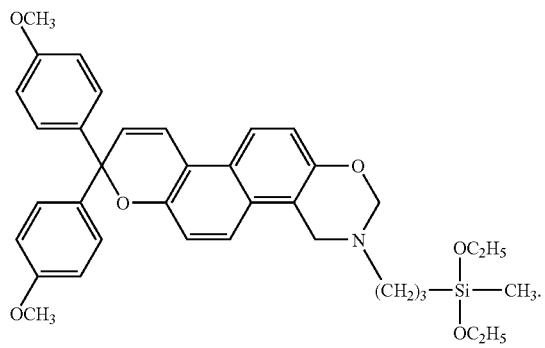

(Ib)

2.05 g of the Compound having formula (XI)-1 obtained as described in Example 2, 0.32 g of formaldehyde, 20 ml of acetonitrile, 1.1 g of 3-aminopropyl-methyldiethoxysilane and 4 g of calcium sulfate are charged into a 50 ml flask equipped with a bubble cooler and magnetic stirrer: the mixture is heated to reflux temperature for 4 hours.

A reaction raw product is obtained, which is cooled to room temperature, washed with toluene (10 ml), filtered and dried under vacuum obtaining a powder.

The above powder is recrystallized with 30 ml of toluene obtaining 0.5 g of a precipitate having a slightly amber-colouring corresponding to the Compound having formula (Ib) which is identified by means of liquid chromatography on a column (HPLC) coupled with a gas-mass (molecular weight=625).

EXAMPLE 5

Evaluation of the Photochromatic Activity.

The photochromatic activities of Compounds (Ia) and (Ib) are evaluated according to the following procedure.

Solutions are prepared at a concentration equal to $10^{-4}$ M (the exact concentrations are indicated in Table 1) of Compounds (Ia) and (Ib) in toluene and 1.3 ml of each solution is subsequently placed in a 1 cm quartz cell having an inlet with a square base.

The quartz cell containing the solution is introduced into a Peltier temperature control system (HP accessory—Nr. HP 89090A), with the possibility of magnetic stirring during the measurement, and is radiated from above with a Philips UVA lamp with irradiation equal to 9 Watt/cm$^2$ resting on the cell itself. The irradiation time is 60" in order to ensure that the maximum colouring degree of the solution is reached.

The spectrum of the solution is registered before and after irradiation between 400 nm and 700 nm with a Hewlett Packard HP 8452A spectrophotometer with photodiodes.

The following data are determined by means of a mathematical calculation effected with the Lotus 123v5w program based on the tristimulus theory:

(a) ($\Delta Y$) which indicates the difference between the light transmittance (Y) of the solution before and after irradiation and represents the photochromatic activity of the compound analyzed at the concentrations indicated in Table 1;

(b) $\Delta L^*$, $\Delta a^*$ and $\Delta b^*$ which correspond to the variation in the colourimetric coordinates of the above solutions CIE 1976 ($L^*$, $a^*$ and $b^*$), corresponding to the gloss or luminosity ($L^*$), to the red-green coordinate ($a^*$) and yellow-blue coordinate ($b^*$), before and after irradiation.

The data obtained are indicated in Table 1.

A further explanation of the above values and information relating thereto can be found, for example, in "Color Science: Concepts and Methods, Quantitative data and Formulae" (1982). G. Wyszecki and W. S. Stiles, 2$^{nd}$ Ed., New York.

TABLE 1

PHOTOCHROMATIC ACTIVITY AND COLOURIMETRIC DATA AT 20° C. IN METHANOL

| Photochromatic Compound | Conc. ($10^{-4}$ M) | $\Delta Y$ | $\Delta L^*$ | $\Delta a^*$ | $\Delta b^*$ |
|---|---|---|---|---|---|
| (Ia) | 1.040 | 14.01 | −6.01 | 10.75 | 1.28 |
| (Ib) | 1.011 | 14.20 | −6.09 | 10.76 | 0.66 |

The invention claimed is:

1. A photochromatic compound belonging to the groups of chromenes and spiro-pyrans having general formula (I):

(I)

[Structure I: chromene-benzoxazine bicyclic system with substituents P, R₄, R₃, O, R₁, R₂, N–R]

wherein:

R represents a linear or branched $C_1$-$C_{10}$ alkyl group,
  wherein said alkyl group is optionally substituted with 1-10 halogen atoms selected from the group consisting of fluorine, chlorine and bromine, hetero-aromatic groups with 5-10 atoms, heterocyclic groups with 5-6 atoms, hydroxyl groups, hydroxyalkyl groups, carboxyl groups, cyano groups, linear $C_1$-$C_6$ alkoxyl groups, branched $C_1$-$C_6$ alkoxyl groups, a 1,2,2,6,6-pentamethylpiperidine group, a vinyl group, a (meth)allyl group, a linear $C_2$-$C_6$ alkenyl group, a branched $C_2$-$C_6$ alkenyl group, an aryl group selected from the group consisting of phenyl, biphenyl and naphthyl,
  wherein said aryl group is optionally substituted with linear or branched $C_1$-$C_6$ alkoxyl groups, carboxyl groups, or N,N-dialkyl-($C_1$-$C_6$)-amine groups, a COOR'$_a$ ester group,
  wherein R'$_a$ represents a linear or branched $C_1$-$C_{10}$ alkyl group, a benzyl group,
  wherein said benzyl group is optionally substituted with 1-5 halogen atoms selected from the group consisting of fluorine, chlorine and bromine, or wherein said benzyl group is optionally substituted with C(X')$_3$ groups, wherein X' is selected from the group consisting of fluorine, chlorine and bromine, or wherein said benzyl group is optionally substituted with linear or branched $C_1$-$C_{10}$ alkyl groups, or wherein said benzyl group is optionally substituted with linear or branched $C_1$-$C_6$ alkoxyl groups, carboxyl groups, cyano groups, or with a 1,2,2,6,6-pentamethylpiperidine group, a linear or branched $C_1$-$C_{10}$ alkyl group substituted with an ORy group,
  wherein Ry represents a linear or branched hydroxy-($C_1$-$C_6$)-alkyl group, a (meth)allyl group, a (meth)acrylic group, a linear or branched carboxy-($C_1$-$C_6$)-alkyl group, an acyloxyl group, or a group having general formula (II):

(II)

[Structure II: R'$_2$–Si(R'$_1$)(R'$_3$)–(CH$_2$)$_n$–NH–C(=O)–]

wherein R'$_1$, R'$_2$ and R'$_3$, the same or different, represent a hydrogen atom a linear or branched $C_1$-$C_{10}$ alkyl group,
  wherein said alkyl group is optionally substituted with 1-10 halogen atoms selected from the group consisting of fluorine, chlorine and bromine, or wherein said alkyl group is optionally substituted with linear or branched $C_1$-$C_6$ alkoxyl groups, carboxyl groups, cyano groups, or with an N,N-dialkyl-($C_1$-$C_6$)-amine group, or with a cyclic amine, a vinyl group, a (meth)allyl group, a linear or branched $C_2$-$C_{10}$ alkenyl group, a COOR'$_a$ ester group,
  wherein R'$_a$ represents a linear or branched $C_1$-$C_{10}$ alkyl group, a linear or branched $C_1$-$C_6$ alkoxyl group, an N,N-dialkyl-($C_1$-$C_6$)-amide group, and n is an integer ranging from 0 to 11, one of the following groups having general formula (III), (IV) or (V):

(III)

[Structure III: –(CH$_2$)$_m$–Si(R'$_4$)(R'$_5$)(R'$_6$)]

(IV)

[Structure IV: phenyl–Si(R'$_4$)(R'$_5$)(R'$_6$)]

(V)

[Structure V: phenyl–O–(CH$_2$)$_m$–Si(R'$_4$)(R'$_5$)(R'$_6$)]

wherein R'$_4$, R'$_5$ and R'$_6$, the same or different, represent a linear or branched $C_1$-$C_{10}$ alkyl group, a linear or branched $C_1$-$C_6$ alkoxyl group, a hydroxyl group, a tri-alkyl-($C_1$-$C_6$)-siloxyl group, or a group having the formula: —O—(CH$_2$)$_2$—O(CH$_2$)$_2$ —OCH$_3$, wherein m is an integer ranging from 1 to 6;

wherein R$_1$, R$_2$, R$_3$ and R$_4$, the same or different, represent a hydrogen atom, a halogen atom selected from the group consisting of fluorine, chlorine, bromine and iodine, a linear or branched $C_1$-$C_{10}$ alkyl group,
  wherein said alkyl group is optionally substituted with 1-10 halogen atoms selected from the group consisting of fluorine, chlorine and bromine, or
wherein said alkyl group is optionally substituted
with linear or branched $C_1$-$C_6$ alkoxyl groups, or
wherein said alkyl group is optionally substituted
with ORx groups, wherein Rx represents a linear
or branched hydroxy-($C_1$-$C_6$)-alkyl group, or
wherein said alkyl group is optionally substituted
with carboxyl groups, hydroxyl groups, cyano
groups, or with a 1,2,2,6,6-pentamethylpiperidine
group, a benzyl group,
  wherein said benzyl group optionally substituted
  with 1-5 halogen atoms selected from the group
  consisting of fluorine, chlorine and bromine, or
  wherein said benzyl group is optionally substi-
  tuted with $C(X')_3$ groups, wherein $X'$ is selected
  from the group consisting of fluorine, chlorine and
  bromine, or wherein said benzyl group is option-
  ally substituted with linear or branched $C_1$-$C_{10}$
  alkyl groups, linear or branched $C_1$-$C_6$ alkoxyl
  groups, carboxyl groups, cyano groups, or with a
  1,2,2,6,6-pentamiethylpiperidine group, a hydroxyl group,
a hydroxy-($C_1$-$C_6$)-alkyl group,
a linear or branched $C_1$-$C_6$ alkoxyl group,
  wherein said alkoxyl group is optionally substituted
  with hydroxyl groups,
an N,N-dialkyl-($C_1$-$C_6$)-amine group,
a piperidine group,
a piperazine group,
a morpholine group,
a $C_1$-$C_6$ carboxyalkyl group,
a $C_2$-$C_6$ carboxyalkenyl group,
a carboxyamide group,
an N,N-dialkyl-($C_1$-$C_6$)-carboxyamide group,
a cyano group,
a nitro group,
a sulfonic group,
an aryl group selected from the group consisting of
phenyl, biphenyl and naphthyl,
  wherein said aryl group is optionally substituted with
  N,N-dialkyl-($C_1$-$C_6$)-amine groups, linear or
  branched $C_1$-$C_6$ alkoxyl groups, hydroxyl groups,
  linear or branched $C_1$-$C_6$ alkyl groups,
an acyl group,
a vinyl group,
a (meth)allyl group,
a (meth)acrylic group,
a heteroallyl group,
a linear or branched $C_2$-$C_6$ alkenyl group,
  wherein said alkenyl group is optionally substituted
  with one or two N,N-dialkyl-($C_1$-$C_6$)-4-aniline
  groups,
an N-2,3-dihydroindoline group,
or a linear or branched $C_1$-$C_6$ thioether group;
  wherein two consecutive substituents between $R_1$,
  $R_2$, $R_3$ and $R_4$ can represent the condensation
  points with other aromatic, heterocyclic or
  quinonic rings,
P represents one of the following groups having general
formula (VI) or (VII):

(VI)

(VII)

wherein $R_5$, $R_6$, $R_7$, $R_8$, $R_9$, $R_{10}$, $R_{11}$ and $R_{12}$, the
  same or different, have the same meanings as the
  $R_1$—$R_4$ substituents described above,
wherein two consecutive substituents between $R_5$
  and $R_{12}$ can represent the condensation points
  with other aromatic, heterocyclic or quinonic
  rings,
wherein Ra represents
a methylene group,
a vinylene group, or
a carbon-carbon bond,
wherein q is 0, 1 or 2;
wherein B and $B_1$ individually, are selected from the
  group consisting of
aryl, phenyl and naphthalene groups,
heterocyclic aromatic groups,
wherein said aryl, phenyl, naphthalene and hetero-
  cyclic aromatic groups are optionally mono, di, or
  tri-substituted substituted with
  hydroxyl groups,
  piperidine groups,
  morpholine groups,
  pyrrole groups,
  linear or branched $C_1$-$C_6$ alkyl groups,
  linear or branched $C_1$-$C_6$ chloro-alkyl groups,
  linear or branched $C_1$-$C_6$ fluoro-alkyl groups,
  linear or branched $C_1$-$C_6$ alkoxyl groups,
  wherein the $C_1$-$C_6$ alkoxy groups are optionally
    substituted with hydroxyl groups,
  linear or branched $C_1$-$C_4$ alkyl groups substituted
    with hydroxyl groups,
  linear or branched $C_1$-$C_6$ alkoxyl groups,
  acryloxyl groups,
  methacryloxyl groups,
  halogen atoms selected from the group consisting
    of chlorine and fluorine,
  groups represented by formulae (VIII) or (IX):

(VIII)

(IX)

wherein E represents a carbon atom or an oxygen
  atom wherein D represents an oxygen atom or a substituted nitrogen atom, on the condition that, when D represents a substituted nitrogen atom, E represents a carbon atom, wherein said nitrogen atom D is substituted with linear or branched $C_1$-$C_6$ alkyl groups, or with $C_2$-$C_6$ acyl groups, wherein $R_{13}$ represents a linear or branched $C_1$-$C_6$ alkyl group, a linear or branched $C_1$-$C_6$ alkoxyl group, a hydroxyl group, or a halogen atom selected from the group consisting of chlorine and fluorine, wherein $R_{14}$ and $R_{15}$ each independently represent a hydrogen atom, or a linear or branched $C_1$-$C_6$ alkyl group, wherein p' is 0, 1 or 2, linear $C_1$-$C_6$ alkyl groups,
branched $C_1$-$C_6$ alkyl groups,
linear $C_1$-$C_6$ chloro-alkyl groups,
branched $C_1$-$C_6$ chloro-alkyl groups,
linear $C_1$-$C_6$ fluoro-alkyl groups,
branched $C_1$-$C_6$ fluoro-alkyl groups,
linear $C_1$-$C_4$ alkyl groups substituted with linear or branched $C_1$-$C_6$ alkoxyl groups,
branched $C_1$-$C_4$ alkyl groups substituted with linear or branched $C_1$-$C_6$ alkoxyl groups,
$C_3$-$C_6$ cycloalkyl groups, wherein the $C_3$-$C_6$ cycloalkyl groups are optionally mono-substituted with a linear or branched $C_1$-$C_6$ alkoxyl group, or wherein the $C_3$-$C_6$ cycloaklyl groups are optionally substituted with a linear or branched $C_1$-$C_6$ alkyl group, or wherein the $C_3$-$C_6$ alkyl groups are optionally substituted with a halogen atom selected from the group consisting of chlorine and fluorine, and a group having general formula (X):

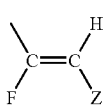

(X)

wherein F represents a hydrogen atom, a linear or branched $C_1$-$C_4$ alkyl group, wherein Z is selected from the group consisting of naphthyl, phenyl, furanyl, and thienyl, wherein said naphthyl, phenyl, furanyl and thienyl groups are optionally mono- or di-substituted with linear or branched $C_1$-$C_4$ alkyl groups, linear or branched $C_1$-$C_4$ alkoxyl groups, or halogen atoms selected from the group consisting of fluorine and chlorine, or, B and $B_1$ considered jointly, are a fluoren-9-ylidene group, wherein said fluoren-9-ylidene group is optionally mono- or di-substituted with linear or branched $C_1$-$C_4$ alkyl groups optionally substituted with hydroxyl groups,
linear or branched $C_1$-$C_4$ alkoxyl groups optionally substituted with hydroxyl groups,
hydroxyl groups,
halogen atoms selected from the group consisting of fluorine and chlorine, or a group selected from spiro-monocyclic $C_3$-$C_{12}$ saturated hydrocarbon rings.

2. The photochromatic compound according to claim 1, wherein R represents one of the following groups:
methyl,
ethyl,
isopropyl,
2-(meth)allyl,
2.-carboxymethyl,
phenyl,
4-N,N-dimethylamino-aniline,
4-methoxybenzene,
4-cyanobenzene,
2-methoxyethyl (—$CH_2CH_2OCH_3$),
hydroxyalkyl,
an alkyl group substituted with an ORy group,
wherein Ry represents a (meth)acrylic group,
a group having general formula (II)

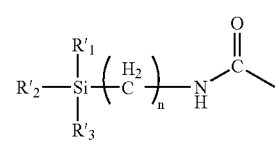

(II)

wherein $R'_1$, $R'_2$ and $R'_3$, the same or different, represent a methoxyl group or an ethoxyl group, and wherein n is 3, a group having general formula (III), (IV) or (V),

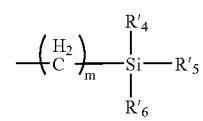

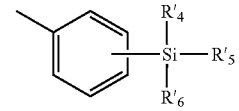

(IV)

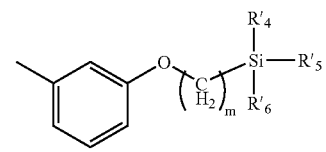

(V)

wherein $R'_4$, $R'_5$ and $R'_6$, the same or different, represent one of the following groups:
methyl,
hydroxyl,
methoxyl,
ethoxyl,
an —O—$(CH_2)_2$—O$(CH_2)_2$—$OCH_3$ group,
or a tri-methylsiloxyl group, and wherein m ranges from 2 to 6;

$R_1$, $R_2$, $R_3$ and $R_4$, the same or different, represent
a hydrogen atom,
a fluorine atom,
a chlorine atom,
a bromine atom,
methyl,
isopropyl, hydroxyl,
2-hydroxyethyl,
methoxyl,
N,N-dimethylamine,
piperidine,
morpholine,
carboxyl,
carboxymethyl,
N,N-dimethyl-carboxyamide,
cyano,
nitro,
methylketone,
phenylketone,
phenyl, or
ORx, wherein Rx represents 2-hydroxyethyl;
P represents one of the groups having general formula (VI) or (VII)

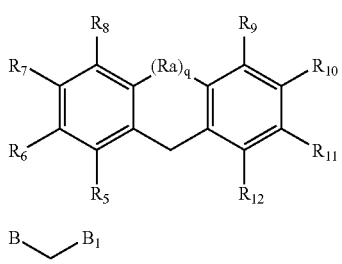

(VI)

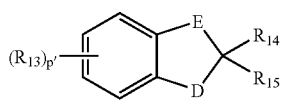

(VII)

wherein:
$R_5$, $R_6$, $R_7$, $R_8$, $R_9$, $R_{10}$, $R_{11}$ and $R_{12}$, have the same meanings as $R_1$, $R_2$, $R_3$ and $R_4$ described above,
wherein two consecutive substituents between $R_3$ and $R_{10}$ can represent the condensation point with other aromatic, heterocyclic or quinonic rings,
wherein Ra represents a carbon-carbon bond, and
wherein q is 0;
wherein
B and $B_1$, are each independently selected from the group consisting of:
phenyl groups,
heterocyclic aromatic groups wherein said phenyl and heterocyclic aromatic groups are optionally mono- or di-substituted with hydroxyl groups,
linear or branched $C_1$-$C_3$ alkyl groups,
$C_1$-$C_2$ hydroxyalkyl groups,
linear or branched $C_1$-$C_3$ alkoxyl groups, or
halogen atoms selected from the group consisting of chlorine and fluorine; and
groups represented by general formula (VIII)

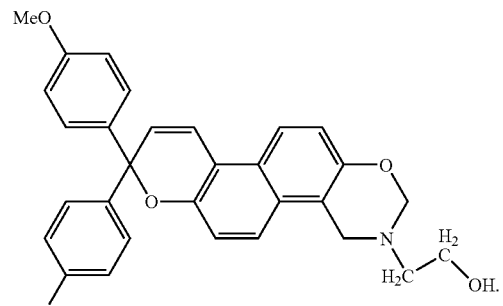

(VIII)

wherein E represents a carbon atom,
wherein D an oxygen atom,
wherein $R_{13}$ represents
a linear or branched $C_1$-$C_3$ alkyl group, or
a linear or branched $C_1$-$C_3$ alkoxyl group;
wherein $R_{14}$ and $R_{15}$ each independently represent a hydrogen atom, or a linear or branched $C_1$-$C_3$ alkyl group,
wherein p' is 0 or 1; or
wherein B and B' considered jointly, represent a fluoren-9-ylidene group, or a moiety selected from the group consisting of:
adamantylidene, bornylidene, norborny-lidene, and bicyclo[3.3.1]nonan-9-ylidene.

3. A photochromatic compound having general formula (I) according to claim 1, corresponding to Compound (Ia):

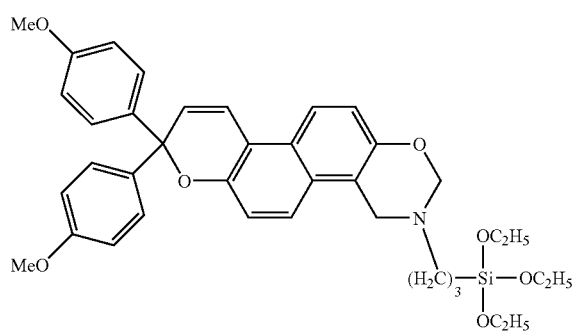

(Ia)

4. A photochromatic compound having general formula (I) according to claim 1 or 2, corresponding to Compound (Ib):

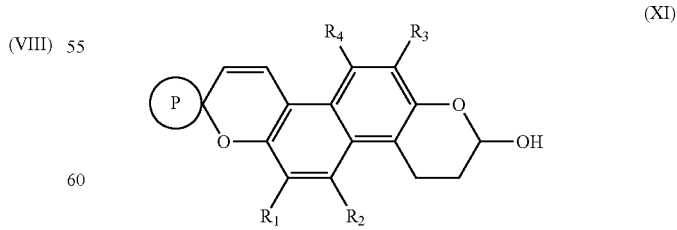

(Ib)

5. A process for the preparation of the photochromatic compounds having general formula (I) according to claim 1, comprising
condensing at least one photochromatic compound having general formula (XI):

(XI)

wherein $R_1$, $R_2$, $R_3$ and $R_4$, the same or different, represent
a hydrogen atom,
a halogen atom selected from the group consisting of fluorine, chlorine, bromine and iodine, a linear or branched $C_1$-$C_{10}$ alkyl group,
   wherein said alkyl group is optionally substituted with 1-10 halogen atoms selected from the group consisting of fluorine, chlorine and bromine, or wherein said alkyl group is optionally substituted with linear or branched $C_1$-$C_6$ alkoxyl groups, or wherein said alkyl group is optionally substituted with ORx groups, wherein Rx represents a linear or branched hydroxy-($C_1$-$C_6$)-alkyl group, or wherein said alkyl group is optionally substituted with carboxyl groups, hydroxyl groups, cyano groups, or with a 1,2,2,6,6-pentamethylpiperidine group,
a beuzyl group,
   wherein said benzyl group optionally substituted with 1-5 halogen atoms selected from the group consisting of fluorine, chlorine and bromine, or wherein said benzyl group is optionally substituted with $C(X')_3$ groups, wherein X' is selected from the group consisting of fluorine, chlorine and bromine, or wherein said benzyl group is optionally substituted with linear or branched $C_1$-$C_{10}$ alkyl groups, linear or branched $C_1$-$C_6$ alkoxyl groups, carboxyl groups, cyano groups, or with a 1,2,2,6,6-pentamethylpiperidine group,
a hydroxyl group,
a hydroxy-($C_1$-$C_6$)-alkyl group,
a linear or branched $C_1$-$C_6$ alkoxyl group,
   wherein said alkoxyl group is optionally substituted with hydroxyl groups,
an N,N-dialkyl-($C_1$-$C_6$)-amine group,
a piperidine group,
a piperazine group,
a morpholine group,
a $C_1$-$C_6$ carboxyalkyl group,
a $C_2$-$C_6$ carboxyalkenyl group,
a carboxyamide group,
an N,N-dialkyl-($C_1$-$C_6$)-carboxyamide group,
a cyano group,
a nitro group,
a sulfonic group,
an aryl group selected from the group consisting of phenyl, biphenyl and naphthyl,
   wherein said aryl group is optionally substituted with N,N-dialkyl-($C_1$-$C_6$)-amine groups, linear or branched $C_1$-$C_6$ alkoxyl groups, hydroxyl groups, linear or branched $C_1$-$C_6$ alkyl groups,
an acyl group,
a vinyl group,
a (meth)allyl group,
a (meth)acrylic group,
a heteroallyl group,
a linear or branched $C_2$-$C_6$ alkenyl group,
   wherein said alkenyl group is optionally substituted with one or two N,N-dialkyl-($C_1$-$C_6$)-4-aniline groups,
an N-2,3-dihydroindoline group,
or a linear or branched $C_1$-$C_6$ thioether group;
   wherein two consecutive substituents between $R_1$, $R_2$, $R_3$ and $R_4$ can represent the condensation points with other aromatic, heterocyclic or quinonic rings,
and wherein P
represents one of the following groups having general formula (VI) or (VII):

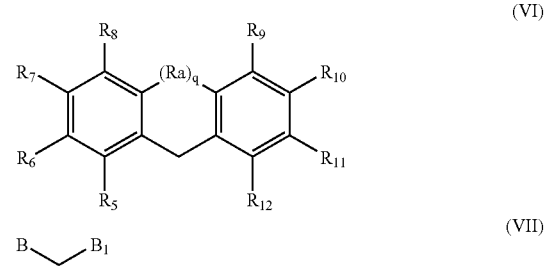

(VI)

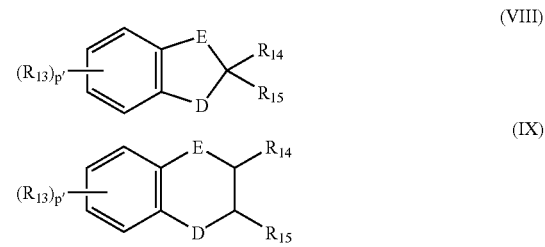

(VII)

wherein $R_5$, $R_6$, $R_7$, $R_8$, $R_9$, $R_{10}$, $R_{11}$ and $R_{12}$, the same or different, have the same meanings as the $R_1$-$R_4$ substituents described above,
wherein two consecutive substituents between $R_5$ and $R_{12}$ can represent the condensation points with other aromatic, heterocyclic or quinonic rings,
wherein Ra represents
a methylene group,
a vinylene group, or
a carbon-carbon bond,
wherein q is 0, 1 or 2;
wherein B and $B_1$ individually, are selected from the group consisting of aryl, phenyl and naphthalene groups,
heterocyclic aromatic groups, wherein said aryl, phenyl, naphthalene and heterocyclic aromatic groups are optionally mono, di, or tri-substituted substituted with
   hydroxyl groups,
   piperidine groups,
   morpholine groups,
   pyrrole groups,
   linear or branched $C_1$-$C_6$ alkyl groups,
   linear or branched $C_1$-$C_6$ chloro-alkyl groups,
   linear or branched $C_1$-$C_6$ fluoro-alkyl groups,
   linear or branched $C_1$-$C_6$ alkoxyl groups,
      wherein the $C_1$-$C_6$ alkoxy groups are optionally substituted with hydroxyl groups,
   linear or branched $C_1$-$C_4$ alkyl groups substituted with hydroxyl groups,
   linear or branched $C_1$-$C_6$ alkoxyl groups,
   acryloxyl groups,
   methacryloxyl groups,
   halogen atoms selected from the group consisting of chlorine and fluorine,
groups represented by formulae (VIII) or (IX):

(VIII)

(IX)

wherein E represents a carbon atom or an oxygen atom,
wherein D represents an oxygen atom or a substituted nitrogen atom, on the condition that, when D represents a substituted nitrogen atom, E represents a carbon atom,
wherein said nitrogen atom D is substituted with linear or branched $C_1$-$C_6$ alkyl groups, or with $C_2$-$C_6$ acyl groups,
wherein $R_{13}$ represents a linear or branched $C_1$-$C_6$ alkyl group, a linear or branched $C_1$-$C_6$ alkoxyl group, a hydroxyl group, or a haloaen atom selected from the group consisting of chlorine and fluorine,
wherein $R_{14}$ and $R_{15}$ each independently represent a hydrogen atom, or a linear or branched $C_1$-$C_6$ alkyl aroup,
wherein p' is 0, 1 or 2,
linear $C_1$-$C_6$ alkyl groups,
branched $C_1$-$C_6$ alkyl groups,
linear $C_1$-$C_6$ chloro-alkyl groups,
branched $C_1$-$C_6$ chloro-alkyl groups,
linear $C_1$-$C_6$ fluoro-alkyl groups,
branched $C_1$-$C_6$ fluoro-alkyl groups,
linear $C_1$-$C_4$ alkyl groups substituted with linear or branched $C_1$-$C_6$ alkoxyl groups,
branched $C_1$-$C_4$ alkyl groups substituted with linear or branched $C_1$-$C_6$ alkoxyl groups,
$C_3$-$C_6$ cycloalkyl groups,
wherein the $C_3$-$C_6$ cycloalkyl groups are optionally mono-substituted with a linear or branched $C_1$-$C_6$ alkoxyl group, or wherein the $C_3$-$C_6$ cycloaklyl groups are optionally substituted with a linear or branched $C_1$-$C_6$ alkyl group, or wherein the $C_3$-$C_6$ alkyl groups are optionally substituted with a halogen atom selected from the group consisting of chlorine and fluorine, and
a group having general formula (X):

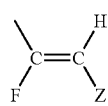
(X)

wherein F represents a hydrogen atom, a linear or branched $C_1$-$C_4$ alkyl group,
wherein Z is selected from the group consisting of naphthyl, phenyl, furanyl, and thienyl,
wherein said naphthyl, phenyl, furanyl and thienyl groups are optionally mono- or di-substituted with linear or branched $C_1$-$C_4$ alkyl groups, linear or branched $C_1$-$C_4$ alkoxyl groups, or halogen atoms selected from the group consisting of fluorine and chlorine, or
B and $B_1$ considered jointly, are
a fluoren-9-ylidene group, wherein said fluoren-9-ylidene group is optionally mono- or di-substituted with
linear or branched $C_1$-$C_4$ alkyl groups optionally substituted with hydroxyl groups,
linear or branched $C_1$-$C_4$ alkoxyl groups optionally substituted with hydroxyl groups,
hydroxyl groups,
halogen atoms selected from the group consisting of fluorine and chlorine, or a group selected from spiro-monocyclic $C_3$-$C_{12}$ saturated hydrocarbon rings with at least one amine having general formula (XII):

$H_2N-R$ (XII)

wherein R
represents
a linear or branched $C_1$-$C_{10}$ alkyl group,
wherein said alkyl group is optionally substituted with 1-10 halogen atoms selected from the group consisting of fluorine, chlorine and bromine,
hetero-aromatic groups with 5-10 atoms,
heterocyclic groups with 5-6 atoms,
hydroxyl groups,
hydroxyalkyl groups,
carboxyl groups,
cyano groups,
linear $C_1$-$C_6$ alkoxyl groups,
branched $C_1$-$C_6$ alkoxyl groups,
a 1,2,2,6,6-pentamethylpiperidine group,
a vinyl group,
a (meth)allyl group,
a linear $C_1$-$C_6$ alkenyl group,
a branched $C_1$-$C_6$ alkenyl group,
an aryl group selected from the group consisting of phenyl, biphenyl and naphthyl,
wherein said aryl group is optionally substituted with linear or branched $C_1$-$C_6$ alkoxyl groups, carboxyl groups, or N,N-dialkyl-($C_1$-$C_6$)-amine groups,
a COOR'$_a$ ester group,
wherein R'$_a$ represents a linear or branched $C_1$-$C_{10}$ alkyl group,
a benzyl group,
wherein said benzyl group is optionally substituted with 1-5 halogen atoms selected from the group consisting of fluorine, chlorine and bromine, or wherein said benzyl group is optionally substituted with C(X')$_3$ groups, wherein X' is selected from the group consisting of fluorine, chlorine and bromine, or wherein said benzyl group is optionally substituted with linear or branched $C_1$-$C_{10}$ alkyl groups, or wherein said benzyl group is optionally substituted with linear or branched $C_1$-$C_6$ alkoxyl groups, carboxyl groups, cyano groups, or with a 1,2,2,6,6-pentamethylpiperidine group,
a linear or branched $C_1$-$C_{10}$ alkyl group substituted with an ORy group,
wherein Ry represents a linear or branched hydroxy-($C_1$-$C_6$)-alkyl group, a (meth)allyl group, a (meth)acrylic group, a linear or branched carboxy-($C_1$-$C_6$)-alkyl group, an acyloxyl group, or a group having general formula (II):

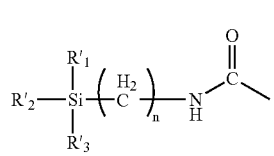
(II)

wherein R'$_1$, R'$_2$ and R'$_3$, the same or different, represent a hydrogen atom a linear or branched $C_1$-$C_{10}$ alkyl group,
wherein said alkyl group is optionally substituted with 1-10 halogen atoms selected from the group consisting of fluorine, chlorine and bromine, or wherein said alkyl group is optionally substituted with linear or branched $C_1$-$C_6$ alkoxyl groups, carboxyl groups, cyano groups, or with an N,N-dialkyl-($C_1$-$C_6$)-amine group, or with a cyclic amine,
a vinyl group,
a (meth)allyl group,
a linear or branched $C_2$-$C_{10}$ alkenyl group,
a COOR'$_a$ ester group,
  wherein R'$_a$ represents a linear or branched $C_1$-$C_{10}$ alkyl group,
a linear or branched $C_1$-$C_6$ alkoxyl group,
an N,N-dialkyl-($C_1$-$C_6$)-amide group,
  and n is an integer ranging from 0 to 11,
one of the following groups having general formula (III), (IV) or (V):

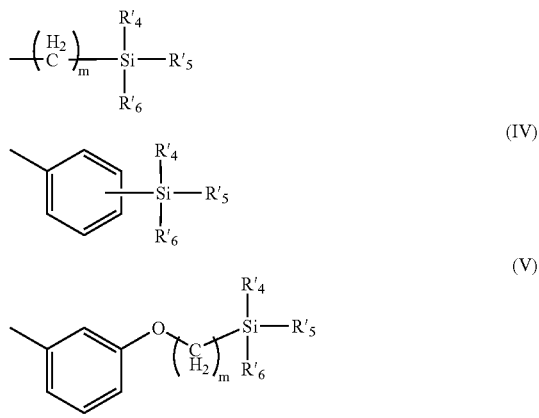

wherein R'$_4$, R'$_5$ and R$_6$, the same or different, represent a linear or branched $C_1$-$C_{10}$ group,
a linear or branched $C_1$-$C_6$ alkoxyl group,
a hydroxyl group,
a tri-alkyl-($C_1C_6$)-siloxyl group,
or a group having the formula: —O—$(CH_2)_2$—O $(CH_2)_2$ —$OCH_3$,
wherein m is an integer ranging from 1 to 6;
in the presence of formaldehyde, an inert organic solvent, at a temperature ranging from 50° C. to 80° C., for a time ranging from 1 hour to 15 hours.

6. The process according to claim 5, wherein the inert organic solvent is selected from the group consisting of ethanol and acetonitrile.

7. The process according to claim 5, wherein the at least one amine having general formula (II) is selected from the group consisting of 2-hydroxyethylamine, 3-hydroxypropylamine, 3-amino-propylmethyldiethoxysilane, p-aminophenyltrimeth-oxysilane, and 3-(2-aminophenoxy)propyltrimethoxysilane.

8. The process according to claim 5, wherein the temperature is 60° C.

9. The process according to claim 5, wherein the reaction time ranges from 1 to 6 hours.

10. A polymeric composition comprising at least one photochromatic compound having general formula (I), according to claim 1, and at least one polymer selected from the group consisting of high density polyethylene, low density polyethylene, ethylene-vinylacetate copolymer, polyether amides, polypropylene, polymethyl methacrylate, polyvinyl alcohol, polyvinyl butyral, cellulose acetate butyrate, epoxy, polysiloxane resins, urethane resins, polycarbonate, polydiethylene glycol bis(allyl carbonate), polyamides, polyesters, polystyrene, polyvinylchloride, polyethylacrylate, siliconic polymers, and mixtures thereof.

11. A coating composition comprising at least one hybrid polysiloxane, silica gel, or at least one hybrid polysiloxane and silica gel, and at least one photochromatic compound having general formula (I) according to claim 1.

12. The composition of claim 10, further comprising at least one additive, wherein the at least one additive is selected from the group consisting of phenolic antioxidants, sterically hindered amines, benzotriazoles, benzophenones, phosphates, phosphonites, enamines, and combinations thereof.

13. A method of making a photochromatic article comprising forming the photochromatic article with the composition of claim 10.

14. A mixture comprising at least one photochromatic compound having the general formula (I) according to claim 1 and at least one photochromatic compound selected from the group consisting of spiro-indoline-oxazines and spiropyrans.

* * * * *